United States Patent
Michaud (10) Patent No.: US 11,040,081 B2
(45) Date of Patent: Jun. 22, 2021

(54) USE OF LOW MOLECULAR WEIGHT COLLAGEN HYDROLYSATE FOR PREVENTING AND/OR REDUCING JOINT PAIN, LATERAL MENISCAL PROTUSION AND/OR IMPROVING CARTILAGE ABRASION GRADE

(71) Applicant: CORPORATION GENACOL CANADA INC., Québec (CA)

(72) Inventor: Guy Michaud, Québec (CA)

(73) Assignee: CORPORATION GENACOL CANADA INC., Blainville (CA)

( * ) Notice: Subject to any disclaimer, the term of this patent is extended or adjusted under 35 U.S.C. 154(b) by 0 days.

(21) Appl. No.: 16/463,985

(22) PCT Filed: Nov. 24, 2017

(86) PCT No.: PCT/CA2017/051415
§ 371 (c)(1),
(2) Date: May 24, 2019

(87) PCT Pub. No.: WO2018/094531
PCT Pub. Date: May 31, 2018

(65) Prior Publication Data
US 2020/0078435 A1 Mar. 12, 2020

Related U.S. Application Data

(60) Provisional application No. 62/426,908, filed on Nov. 28, 2016.

(30) Foreign Application Priority Data

Nov. 28, 2016 (CA) ..................................... 2950096

(51) Int. Cl.
*A61K 38/00* (2006.01)
*A61K 38/01* (2006.01)
*A61P 19/02* (2006.01)

(52) U.S. Cl.
CPC ............ *A61K 38/014* (2013.01); *A61P 19/02* (2018.01)

(58) Field of Classification Search
CPC ................................ A61K 38/12; A61K 45/06
See application file for complete search history.

(56) References Cited

U.S. PATENT DOCUMENTS

| 8,778,422 B2 * | 7/2014 | Oesser | .................... A61P 21/00 424/765 |
| 2007/0196438 A1 * | 8/2007 | Escaich | ................ A61K 31/737 424/439 |

OTHER PUBLICATIONS

International Search Report and Written Opinion dated Jan. 25, 2018 from International Application No. PCT/CA2017/051415 (Authorized officer, Antonio Candeliere), 7 pages.
Bruyére et al., "Effect of collagen hydrolysate in articular pain: A 6-month randomized, double-blind, placebo controlled study", Complementary Therapies in Medicine, Jun. 2012, vol. 20, No. 3, pp. 124-130.
Bernardo et al., "A randomized controlled trial on the effects of oral collagen treatment on the medial knee joint space and functional outcome among veterans memorial medical center patients diagnosed with osteoarthritis of the knee", PARM Proceedings, Jan. 2012, vol. 4, No. 1, pp. 1-8.
Feliciano et al., "Effect of collagen hydrolysate as adjuvant treatment to exercise for knee osteoarthritis", PARM Proceedings, Feb. 2017, pp. 4-17.

* cited by examiner

*Primary Examiner* — Jeanette M Lieb
(74) *Attorney, Agent, or Firm* — MH2 Technology Law Group, LLP (57) ABSTRACT

The invention provides the use of low molecular weight collagen hydrolysate for reducing joint pain such as in arthritis or osteoarthritis.

22 Claims, 2 Drawing Sheets

Figure 1 Proportion of clinical responders at 6 months according to VAS.

Figure 2. Graphical Representation of the WOMAC Scores

Figure 3
Musculoskeletal Ultrasound Protocol for the Knee (Bernardo et al. 2014)
1. ARTICULAR CARTILAGE
   a. Transverse anterior view
      i. Patient supine with knee fully flexed
      ii. Position transducer immediately above the patella, perpendicular to the long axis of the extremity with the depth and focal zone optimised to visualize the trochlear articular cartilage on the medial trochlea, trochlear notch and lateral trochlea on the same axial image.
      iii. Divide the image into three, zooming in on the image to enhance visualization.
      iv. Measure the narrowest cartilage thickness in three locations: medial, lateral and central/trochlear notch. Each measurement will be done three times.
      v. Evaluate the clarity and grade of the femoral hyaline cartilage
   b. Longitudinal sagittal view
      i. Knee flexed at 90 degrees
      ii. Position transducer longitudinally close to the medial/lateral border of the patella as possible
      iii. Measure the narrowest portion of the articular cartilage at the medial longitudinal and lateral longitudinal planes. Each measurement will be done 3 times.
      iv. Evaluate the clarity and grade of the femoral hyaline cartilage
2. SUPRAPATELLAR AND INFRAPATELLAR RECESS
   a. Suprapatellar recess
      i. Knee flexed 45 degrees
      ii. Scan for effusion and/or synovitis. If with effusion, perform compression test and measure largest anteroposterior diameter 3 times.
   b. Infrapatellar recess
      i. Knee flexed 30 degrees
      ii. Scan for effusion and/or synovitis over the superficial and deep infrapatellar areas. If with effusion, perform compression test and measure largest anteroposterior diameter 3 times.
   c. Evaluate the degree of synovitis
   d. Evaluate the power Doppler signal of the synovial membrane in relation to the surrounding tissue of the quadriceps muscle by placing the transducer head on the suprapatellar and infrapatellar recesses for 10 secs.
3. MEDIAL AND LATERAL MENISCUS
   a. Knee flexed at 10 degrees
   b. Internal rotation and mild varus stress to examine the lateral meniscus; external rotation and mild valgus stress to examine the medial meniscus.
   c. Measure meniscal protrusion 3 times.
4. PES ANSERINE BURSITIS
   a. Knee fully extended
   b. If a bursitis is found, measure the largest anteroposterior diameter 3 times and evaluate power Doppler signal
5. BAKER'S CYST
   a. Patient in prone position.
   b. Position transducer head at the level of the midcalf in the transverse plane and visualize the medial gastrocnemius, lateral gastrocnemius and soleus muscles.
   c. Continue scanning superiorly to the level of the knee joint with visualization of the semimembranosus tendon medial to the gastrocnemius tendon. If there is a Baker's cyst found, measure the widest transverse diameter in short axis 3 times.

USE OF LOW MOLECULAR WEIGHT COLLAGEN HYDROLYSATE FOR PREVENTING AND/OR REDUCING JOINT PAIN, LATERAL MENISCAL PROTUSION AND/OR IMPROVING CARTILAGE ABRASION GRADE

CROSS-REFERENCE TO RELATED APPLICATIONS

This application is a U.S. National Stage application of PCT/CA2017/051415 filed 24 Nov. 2017, which claims priority to U.S. Provisional Patent Application No. 62/426,908 filed 28 Nov. 2016 and Canadian Application No. 2950096 filed 28 Nov. 2016, the entire disclosures of which are incorporated herein by reference.

TECHNICAL FIELD

The technical field generally relates to the use of low molecular weight collagen hydrolysate of the invention for limiting the cartilage thickness loss, preventing and/or reducing joint pain such as in arthritis or osteoarthritis. This could be achieved by improvement of cartilage abrasion grade and, in the knee, by reduction of lateral meniscal protrusion.

BACKGROUND

Joint pain is a major cause of disability in subjects aged more than 50 years, two out of three subjects affected by arthritis are women. Symptomatic pain relief can be obtained with analgesics such as paracetamol, or non-steroidal anti-inflammatory drugs. These treatments, while generally safe when used at low doses and for short terms, can result in serious complications (gastrointestinal bleeding, renal failure, coronary heart disease) when used for long-terms or at higher doses and could obviously reduce the adherence to therapy.

Osteoarthritis is the most common form of arthritis. The main difference between osteoarthritis and rheumatoid arthritis is the cause behind the joint symptoms. Osteoarthritis is caused by mechanical wear and tear on joints. Rheumatoid arthritis is an autoimmune disease in which the body's own immune system attacks the body's joints. Osteoarthritis is a degenerative joint disease characterized by progressive destruction of joint cartilage and associated structures such as bone, synovial and fibrous joint capsule and the periarticular musculature. It is a most disabling musculoskeletal disorder. It is likely to be a frequent problem for physiatrists who have outpatient musculoskeletal practices. The disease accounts for 25% of visits to primary care physicians. Approximately 27 million Americans and 5 million Canadian adults report having arthritis. Epidemiologic surveys estimate that 30-40% of adults have some radiographic evidence of osteoarthritis, with at least one fourth of those having moderate or severe disease.

Symptoms often begin on one side of the body and may spread to the other side. Symptoms begin gradually and are often limited to one set of joints, usually the finger joints closest to the fingernails or the thumbs, large weight-bearing joints (hips, knees), or the spine. Morning stiffness lasts less than 1 hour. Stiffness returns at the end of the day or after periods of activity. Osteoarthritis causes pain but also depression, anxiety, feelings of helplessness, limits activities of daily living and productivity, leads to disability, loss of everyday family joys and responsibilities. Because of these impairments, osteoarthritis-related disability creates huge costs for individuals, their families, and the nation. The impact on disability attributable to knee osteoarthritis is similar to that due to cardiovascular disease and greater than that caused by any other medical condition in the elderly. Although younger adults develop osteoarthritis secondarily from injury and loss of biomechanical integrity, osteoarthritis most often occurs in the aging adult. The incidence and prevalence increased 2- to 10-fold from 30-65 years of age, and it increased further beyond 65 years. It is projected that the number of people with arthritis will further increase due to longer life expectancy. The causes are multifactorial and the risk factors differ for every joint. Although any synovial joint can be affected, osteoarthritis occurs most frequently in the knee, hip, hand, and spinal apophyseal joints. There is increasing acknowledgment that osteoarthritis, particularly in the knee, can be regarded as a whole-organ degenerative process, with an emphasis on the contribution of multiple articular and periarticular abnormalities in the clinical expression of the disease. Common risk factors include increasing age, obesity, previous joint injury, overuse of the joint, weak thigh muscles, and genes.

The impact of osteoarthritis is a cause for concern. There is a need for an effective treatment for the millions of people with osteoarthritis. Currently, there is no single drug that results in reversal or prevention of osteoarthritic changes. If joints show signs of degenerative disease, treatment is typically aimed only at relieving pain and inflammation, the last resort being usually surgery, either for smoothing the edges of the joint cartilage or replacing the damaged joint with an artificial one. Management of the disease is focused on reducing pain, maintaining mobility, and minimizing disability with the use of nonspecific symptomatic agents like non-steroidal anti-inflammatory drugs (NSAIDs) which although have no effect on osteoarthritis itself; can be effective in relieving pain due to inflammation. However, these NSAIDs have various adverse reactions like gastrointestinal complications, and can have various drug interactions with the other medications taken by most of the elderly patients. Depot glucocorticoids can have a pain-reducing effect over several weeks if given by intra- or periarticular injection. In animal experiments, however it was shown that glucocorticoids can attack joint cartilage; thus, it can only be given at most two to three times a year to the same joint. Physiotherapy is an important aspect in the complex treatment of osteoarthritis. It focuses on function and postural training, range of motion and strengthening exercises, and application of heat or cold for pain relief. Some patients in the general population are turning to alternative medicine for more natural treatments, such as food supplements and over-the-counter products, but the proprieties of these products are not always based on scientific evidence on their potency and/or depend on the specific extracts of natural products. The quantity to be absorbed by the patient may be large (over 10 000 mg/day).

The articular cartilage is comprised of chondrocytes and an extracellular matrix which is maintained by the chondrocytes. The macromolecular framework of articular cartilage consists of collagens (predominantly type II collagen), proteoglycans, and non-collagenous proteins. This matrix provides the cartilage with its tensile stiffness and strength. The proteoglycans create the osmotic swelling pressure that is responsible for compressibility and elasticity of cartilage counteracted by the resistance of the intact collagen fibrils. Collagens contribute about 60-70% to the dry weight of the cartilage while proteoglycans provide 25-35%, and non-collagenous proteins and glycoproteins contribute 15-20%.

The disruption of the structural integrity of articular cartilage, its deterioration, and its eventual loss are a result of an imbalance between anabolic and catabolic activity in the cartilage tissue. The most common origins of this imbalance include chondrocyte senescence and pathophysiologic conditions such as osteoarthritis.

It seems that the primary change in osteoarthritis begins in the cartilage. There is an apparent change in the arrangement and size in the collagen fibers. The biomechanical data are consistent with the presence of a defect in the collagen network of the cartilage, perhaps due to disruption of the "glue" that binds adjacent fibers together in the matrix.

The main components of cartilage are the collagen fibers that provide its structural framework and stability and the so-called proteoglycans that surround these fibers, furnishing them with elasticity and support. In healthy cartilage, these substances are constantly being synthesized and broken down. These processes, however, occur in equilibrium. In osteoarthritis, the equilibrium shifts significantly toward breakdown, thus leading to a continuous loss of cartilage mass. The spaces that are created are subsequently filled with less elastic collagen fibers, and these in turn increase the susceptibility of the cartilage to injury. This initiates the process that leads to osteoarthritis, where, in the worst case, the cartilage becomes completely degraded and exposes the underlying bone material.

It has been theorized that new treatments should focus on improving the health of this existing joint collagen. Collagen products are recognized as safe components of pharmaceuticals and foods by the US Food and Drug Administration (FDA) Center for Food Safety and Nutrition and was designated as "Generally Recognized As Safe" (GRAS).

Collagen is a large protein. It is the main structural protein in the extracellular space in the various connective tissues in animal bodies. It is found in animals exclusively. Collagen is not a uniform substance but is rather a family of proteins. There are more than 20 types of collagen, varying in structure and occurrence, the most frequent being Types I to V. In cartilage, it is mostly type II. It is not soluble in cold or hot water. It has a triple helix structure with three amino acid chains joined together. All collagens are characterized by high content of hydroxyproline and glycine (almost three times the amounts in other proteins), low content of sulphur containing amino acids and absence of tryptophan. This amino acid composition is responsible for the 3D conformation of collagen. Its molecular weight is approximately 300,000 daltons. The largest commercial sources are: beef and pork (skin, hides, bone), fish skins and scales. It is mostly found in the flesh and connective tissues. It is almost always present in by-products of commercial processing. Contrary to the long-held opinion that gelatine is fully digested in the intestinal tract, scientists know today that some fragments of the gelatine can pass through the intestinal membrane unaltered (Schrieber et al., 2007).

Gelatin is extracted from collagen sources, usually pretreated with acid or alkali to break down connective structure and to render the material soluble in warm or hot water. Subsequent filtration, ion exchange and drying yields a dry crystalline granule or powder which is soluble in hot water but insoluble in cold water. This process also purifies the collagen protein by removing fat, salts, carbohydrates and non-collagen proteins. Thus, the triple helix structure is broken down and replaced by single chains of amino acids. Its average molecular weight is 100,000 daltons. Gelatin can form a gel in aqueous solutions.

Collagen Hydrolysate (CH) is further made from gelatin by enzymatic digestion to hydrolyse peptide bonds of the gelatin. Selection of enzymes, time, temperature and pH enable to control digestion of the gelatin chains to a mixture of lower molecular weight chains. Collagen hydrolysate contains peptides with different chain lengths or molecular weights, which are produced during the enzymatic hydrolysis. Collagen hydrolysate thus can provide the building blocks necessary for the synthesis of the cartilage matrix. Typical collagen hydrolysates are completely water soluble and have average molecular weights in the range of 2000-5000 daltons. The term Ultra Low Molecular Weight Hydrolysate may be used for materials below 2000 daltons. If the low molecular collagen hydrolysate is further digested, the lower molecular weight chains will provide polypeptides, i.e. very low molecular weight digests, and even tripeptides or dipeptides depending on the number of amino acid residues.

Commercially available collagen hydrolysates such as Peptan™ (Darling) and Fortigel™ (Gelita) have a molecular weight of 2000-5000 Da (EP 1 885 771, CA 2 854 856, U.S. Pat. No. 9,072,724, WO 2013/079373). Subjects need to take about 10 g/day of these collagen hydrolysates before beneficing from any improvement, such as promoting skin elasticity, suppleness and hydratation. There is a need for lower dosages of collagen hydrolysate of lower molecular weights for limiting the cartilage thickness loss and preventing and/or reducing joint pain such as in arthritis or osteoarthritis, and/or by improvement of cartilage abrasion grade and, in the knee, by reduction of lateral meniscal protrusion in patients. This is particularly important for elder patients who often already take several pills a day and need to improve patient adherence to treatment regimens is critical. Managing the number of pills to be taken every day is a key factor for patient adherence to their treatment. A less frequent and lower dosage results in better adherence.

SUMMARY

In one embodiment, the invention provides use of a collagen hydrolysate to prevent and/or reduce joint pain in a patient.

In one embodiment, the invention provides use of a collagen hydrolysate to prevent and/or reduce joint pain in osteoarthritis in a patient.

In one embodiment, the invention provides use of a collagen hydrolysate to increase a cartilage abrasion grade and reduction of a lateral meniscal protrusion in a patient's knee.

In one embodiment, the invention provides use of a collagen hydrolysate, wherein the daily dosage of the collagen hydrolysate is between 1000 and 2000 mg, preferably between 1000, 1050, 1100, 1150, 1200, 1250, 1300, 1350, 1400, 1450, 1500, 1550, 1600, 1700, 1800, 1900 and 2000 g, more preferably 1200 mg, or not more than 1200 mg per day.

In one embodiment, the invention provides use of a collagen hydrolysate, wherein the use lasts more than 3 months, more preferably 6 months and even more preferably more than 6 months.

In one embodiment, the invention provides use of a collagen hydrolysate, wherein the collagen hydrolysate has a molecular weight of less than 1500, 1400, 1300, 1200, 1100, 1000, 950, 900, 850, 800, 750, 700, 650 or 600 daltons, preferably less than 1000, 950, 900, 850, 800, 750, 700, 650 or 600 daltons, more preferably 1000 daltons.

In one embodiment, the invention provides use of a collagen hydrolysate, wherein the collagen hydrolysate is in a solid, gel or liquid form.

In one embodiment, the invention provides use of a collagen hydrolysate, wherein the collagen hydrolysate is in a composition comprising a pharmaceutically acceptable excipient, diluent and/or carrier, gelatin, microcrystalline cellulose, silicon dioxide, vegetable magnesium stearate, magnesium stearate, caramel, Citric acid, Glycine, L-Histidine, L-Lysine, L-Methionine, L-isoleucine, leucine, L-phenylalanine, potassium sorbate, purified water, sodium benzoate, sodium citrate, Stévia, natural vanilla flavor, flavor, aroma, and/or a compound improving taste and/or odor.

In one embodiment, the invention provides use of a collagen hydrolysate, wherein the collagen hydrolysate and/or the composition comprising said collagen hydrolysate further comprises include hyaluronic acid, amino acid reissued such as the amino acid GABA, glucosamine, melatonin, MSM, chondroitin, vitamins such as vitamin C, curcuma and/or curcumin.

In one embodiment, the invention provides use of a collagen hydrolysate, wherein the joint pain is shoulder, elbow, hand, lumbar spine, hip or knee pain.

In one embodiment, the invention provides use of a collagen hydrolysate, wherein the collagen hydrolysate is prepared from beef, pork, poultry, or fish skins or scales, preferably from beef or pork.

In one embodiment, the invention provides use of a collagen hydrolysate, wherein the source of collagen is skin, hides, or bone.

In one embodiment, the invention provides use of a collagen hydrolysate, wherein the patient is older than 45, 50, 55, 60, 65, 70, 75, 80, 85, or 90 years.

In one embodiment, the invention provides use of a collagen hydrolysate, wherein the patient is a woman.

In one embodiment, the invention provides use of a collagen hydrolysate, wherein the collagen hydrolysate has no bitter taste or odor.

In one embodiment, the invention provides use of a collagen hydrolysate as defined herein for improving bone health.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

FIG. 3 shows the musculoskeletal ultrasound protocol for the knee (Bernardo et al. 2014).

DETAILED DESCRIPTION

In one embodiment, the present invention may provide a low molecular weight collagen hydrolysate (CH) and/or a composition such collagen hydrolysate and a pharmaceutically acceptable carrier, which improves joint symptoms with an improvement in joint pain and/or physical function symptoms, more particularly caused by osteoarthritis of the shoulder, elbow, hand, lumbar spine, hip or knee pain, more preferably related to aging.

In one embodiment, the present invention may provide a treatment for limiting the cartilage thickness loss by improvement of cartilage abrasion grade in an articulation and, in the knee, by reduction of lateral meniscal protrusion.

In one embodiment, the present invention may provide a treatment for another articulation.

In one embodiment, the collagen hydrolysate or composition comprising such collagen hydrolysate may improve the quality of skin, hair and/or nails In one embodiment, the collagen hydrolysate or composition comprising such collagen hydrolysate may improve bone mineral density of a subject.

In one embodiment, the collagen hydrolysate of the invention is obtained from a Genacol™ product.

In one embodiment, the collagen hydrolysate of the invention is obtained from Type II collagen.

In one embodiment, the collagen hydrolysate of the invention is obtained from cattle, beef, pork (skin, hides, bone), poultry, or fish skins or scales.

In one embodiment, the average molecular weight or molecular weight of the collagen hydrolysate of the invention is lower than 2000 daltons. In one embodiment, it is lower than 1500, 1400, 1300, 1200, 1100, 1000, 950, 900, 850, 800, 750, 700, 650 or 600 daltons. In a preferred embodiment, the molecular weight is 1000 daltons. In another embodiment, the molecular weight is lower than 1000 daltons.

The molecular weight profile of the collagen hydrolysate is dependent on the raw materials and especially the manufacturing process used. Depending on the chosen enzymatic hydrolysis, a collagen hydrolysate can be obtained with a mean molecular weight within a specified range.

Hydrolysate could be manufactured directly from pure or nearly pure collagen. However, this is seldom done because collagen is very resistant. Collagen is resistant to most proteases and requires special collagenases for its enzymatic hydrolysis. This method probably is quite expensive. The collagenous domain is hardly digested by enzymes due to its stable triple helix. The processes involved in processing hydrolysed collagen are first demineralization, extraction of collagen to gelatine, enzymatic hydrolysis to obtain hydrolysed collagen by hydrolysis of peptide bonds of the gelatine molecules, ion exchange, filtration (such as membrane filtration technique), evaporation, sterilization and finally drying.

Frequently, a combination of enzymatic and chemical hydrolysis method is used. In a first step the manufacturer produces gelatine using chemical hydrolysis and then hydrolyzed with enzymes until the desired molecular weight is achieved. These enzymes are proteases from various sources such as animal, plant, yeast or bacterial. They break peptide bonds. They include trypsin, chymotrypsin, pepsin, pancreatin, bromelain (Enzeco), papain, alcalase, propase E, Neutrase, Flavourzyme, Validase, Corolase and Protamex. Each peptidase has a specific hydrolysis profile, in terms of which substrate or amino acids they prefer, conditions of experiments (time, temperature, pH, concentration, ratio substrate/enzyme etc). The enzymes can be exoproteases or endoproteases, such as metalloproteases and/or serine proteases. In one embodiment, the enzymes are obtained from enzymes from the microorganisms *Bacillus subtilis, Bacillus licheniformis, Bacillus amyloliquefaciens, Aspergillus oryzae, Aspergillus sojae* and/or *Aspergillus melleus*. Other enzymes are described in EP 1 885 771 (Gelita).

In order to better achieve the desired result, a mix of enzymes is used either together or sequentially. In one embodiment, the choice and order of application of the enzymes chosen, together with reaction duration (between 1 to 4 hours), pH (between 5 and 6.5) and temperature (between 40 and 70° will allow to obtain a specific CH. The endopeptidases will have an impact on the length/weight of the CH, its amino acid profile and the exopeptidases on the termini of the peptides/CH. In one embodiment, at least 50% of the N-terminal amino acids of the collagen hydrolysate are hydrophobic amino acids, such as alanine, leucine and isoleucine.

Subsequently, the enzymes are thermally deactivated (for instance at 90° C. and/or with hydrogen peroxide) and the solution is spray dried.

The molecular weight distribution of the resultant collagen hydrolysate can be determined by the person of ordinary skill in the art, such as means of gel permeation chromatography, using the following parameters:

Static phase: TSK 2000 SW XL (Tosoh Bioscience GmbH)

Mobile phase: 0.4 mol/l sodium dihydrogen phosphate pH 5.3

Flow rate: 0.5 ml/min

Calibration standard: defined collagen-type I fragments (FILK, Freiberg)

Detection: UV detector Knauer K-2501 at 214 nm.

In one embodiment, the low molecular weight collagen hydrolysate can be part of a food, nutritional, functional, bar, dietary or drink supplement, either solid, gel or liquid.

In one embodiment, it has no bitter taste or odor. It is highly digestible and bioavailable. It is highly absorbed in blood.

In one embodiment, the solid, gel or liquid dosage of the collagen hydrolysate contains 5000, 4000, 3000, 2000, 1500, 1200 or 1000 mg of collagen hydrolysate. It can be in the form of powder, caplets, tablets, soft or hard gel capsules, of 100, 200, 300, 400, 500, 1000 mg each for example.

In one embodiment, the patient takes between 1000 and 2000 mg of collagen hydrolysate per day, more preferably 1000, 1050, 1100, 1150, 1200, 1250, 1300, 1350, 1400, 1450, 1500, 1550, 1600, 1700, 1800, 1900, 2000 mg, either in solid, gel or liquid form. In one embodiment the dosage is 1200 mg or no more than 1200 mg of collagen hydrolysate per day. Health Canada mentions possible adverse effects at dosage higher than 2800 mg of collagen hydrolysate per day, for pregnant or breastfeeding women and/or patients suffering from kidney disease or liver disease and/or patients following a low protein diet.

The treatment can last at least 1 month, 2 months, 3 months, 6 months, 8 months, 10 months, 12 months, 15 months, 18 months, 24 months or more. In one embodiment, the treatment is at least 6 months.

In one embodiment, the collagen hydrolysate of the invention is combined with other ingredients, carriers, excipients, diluents.

In one embodiment, the collagen hydrolysate or composition comprising said collagen hydrolysate of the invention is Genacol—original Formula™, Genacol—Optimum™ (with AST collagen, glucosamine, chondroitin sulfate, MSM), Genacol Plus™ (with glucosamine), Genacol Anti-Inflammatory™ (with curcuma) or Genacol Sleep™ (with melatonin).

In one embodiment, additional ingredients of the composition may include hyaluronic acid, amino acid reissued such as the amino acid GABA, glucosamine, melatonine, MSM, chondroitine, vitamins such as vitamin C, curcuma and/or curcumin.

Non-medicinal ingredients of the composition may include gelatin, microcrystalline cellulose, silicon dioxide, vegetable magnesium stearate, magnesium stearate, caramel, Citric acid, Glycine, L-Histidine, L-Lysine, L-Methionine, L-isoleucine, leucine, L-phenylalanine, potassium sorbate, purified water, sodium benzoate, sodium citrate, Stévia, natural vanilla flavor, flavor, aroma, compound improving taste and/or odor, diluent, excipient, and/or carrier.

Example 1—the Belgium Study

Study Design and Patients' Selection

In this 6-month double-blind randomized controlled trial, subjects received either the collagen hydrolysate of the invention (Genacol, Blainville, QC, Canada) in a daily dosage equivalent to 1200 mg of collagen hydrolysate (i.e. 3 hard gel capsules per day) or a placebo (identical hard gel capsules, to be consumed in the same daily dosage). The randomization list was established with a computer assisted method by blocks of four. (Bruyère O, et al. 2012)

Subjects were included if they were ambulatory males or females aged 50 years or over, with joint pain (hip, knee, elbow, shoulder, hand or/and lumbar spine) over 30 mm on a 0-100 mm visual analogue scale (VAS). The target joint that was followed-up throughout the study was the most painful joint at the inclusion visit. General exclusion criteria included: any intra articular injection, whichever side, during the previous 3 months (6 months for hyaluronic acid) applied at the target joint; clinical evidence or suspicion, at the target joint, of septic arthritis, inflammatory joint disease, gout, Paget's disease of the bone or discal hernia; treatment with a chondroprotective agent (glucosamine sulfate, chondroitin sulfate) during the past 3 months.

Outcomes Assessment

Clinical assessments of the patients were performed at the baseline and after a follow-up of 6 months.

The primary objective of the study was to compare the percentage of responders between the active food supplement group and the placebo group. A responder subject was defined as a subject experiencing a clinically significant improvement (i.e. by 20% or more) in the most painful joint using the VAS score.

Secondary objectives were to compare between the two groups the consumption of pain rescue treatments, the pain/function changes, the health-related quality of life changes, the utility value changes and the tolerability and incidence of any adverse events.

Pain and function were assessed by the Lequesne index (hip and knee), the DASH score (upper arm) and the EIFEL questionnaire (Spine).

The Lequesne index evaluates pain or discomfort at the level of the knee or the hip, the maximum distance walked and activities of daily living. Scores range from 0 to 24, with higher scores indicating greater disease severity. The Lequesne Index questionnaire is well recognized for its adequate validity, reliability, and responsiveness.

The DASH Outcome Measure is a 30-item, self-report questionnaire designed to measure physical function and symptoms in people with any of the several musculoskeletal disorders of the upper limb.

The EIFEL questionnaire, also called the Roland-Morris questionnaire is a self-administered disability measure in which greater levels of disability are reflected by higher numbers on a 24-point scale. The EIFEL questionnaire has been shown to yield reliable measurements, which are valid for inferring the level of disability, and to be sensitive to changes over time for groups of patients with low back pain.

Using these three questionnaires (i.e. Lequesne, DASH and EIFEL), another definition of clinical responder was defined. A responder subject was defined as a subject experiencing a clinically significant improvement in the most painful joint, according to one of the specific questionnaires:

a reduction of at least 25% in Lequesne's index, a reduction of at least 5 points in the EIFEL's score or a reduction of at least 12.7 points in the DASH's score. The percentage of clinical responders in the active treatment group was then compared to that in the placebo group.

The EQ-5D health questionnaire is a generic instrument used to measure utility. It contains a graduated visual analogue scale (VAS) from 0 (worst imaginable health state) to 100 (best imaginable health state).

General health status was measured with the Medical Outcomes Study 36-item short form Health Survey (SF-36). The SF-36 consists of the measure of eight health dimensions (physical function, bodily pain, general health, vitality, mental health, social function, and role of physical and emotional health) in the conduct of daily activities. The SF-36 has been reported to have good validity, internal consistency, and reliability in the assessment of physical and mental health status of subjects and their progression.

Statistical Analysis 200 subjects were planned to be included in this study (100 in each group). This was based on the hypothesis of a difference of at least 40% between the two groups in the proportion of subject being considered as responder. A responder subject was defined as a subject experiencing a clinically significant improvement (i.e. by 20% or more) in the most painful joint using the VAS score. The pre-planned statistical power was fixed at 90%.

Intent-to-treat (ITT) analyses were performed for all randomized patients, using the last observation carried forward approach. Dichotomous variables were reported using percentages. Descriptive statistics were reported as mean and SD for continuous normally distributed variables or as median and quartiles for non-normally distributed variables. Comparisons of categorical variables between collagen hydrolysate and placebo groups were performed with the use of the chi-square test. For continuous variables, the unpaired Student's t test and the Mann-Whitney test were used to compare differences between groups. All results were considered to be statistically significant if the corresponding p value was below 0.05.

Results

Baseline characteristics of the study population are reported in Table 1.

TABLE 1

Baseline characteristics.

| | Collagen hydrolysate (n = 100) | Placebo (n = 100) | p-Value |
|---|---|---|---|
| Age (mean ± SD) | 65.70 ± 7.83 | 64.44 ± 8.5 | 0.27 |
| Gender (female/male %) | 73/27 | 65/35 | 0.22 |
| Clinical characteristics BMI (mean ± SD) | 27.64 ± 4.67 | 27.60 ± 4.59 | 0.96 |
| Target joint (%) | | | |
| Shoulder, elbow, hand | 26% | 22% | |
| Lumbar spine | 27% | 39% | |
| Hip | 13% | 11% | |
| Knee | 34% | 28% | |

Figure 1:
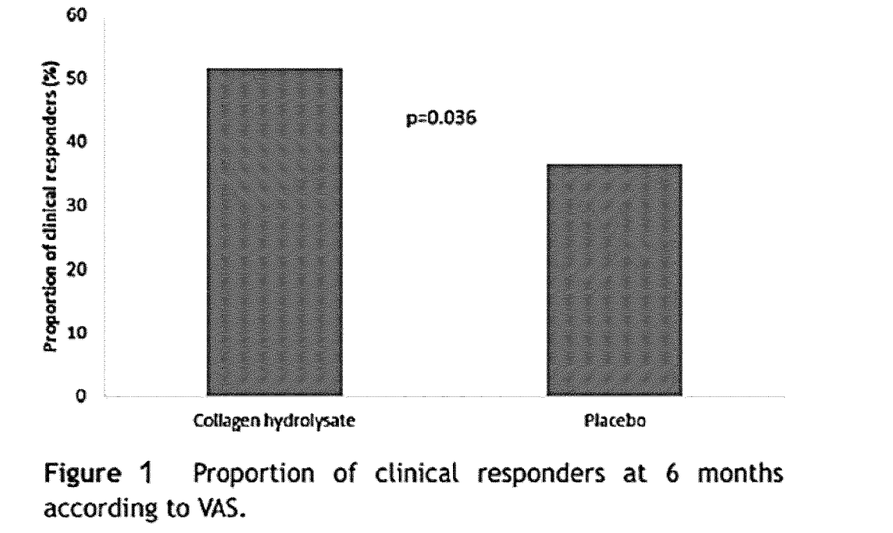
FIG. 1 shows the proportion of clinical responders at 6 months according to VAS.

The number of patients who withdrew for whatever reason from the study was well balanced between the two groups. 56 patients withdrew (33 in the collagen hydrolysate group, 23 in the placebo group):

At 6 months, the proportion of clinical responders according to the VAS was significantly higher in the collagen hydrolysate group (51.6%) than in the placebo group (36.5%) (p=0.036) (FIG. 1).

We also looked at the proportion of clinical responders at 6 months according to the VAS by target joint (Table 2). Although it did not reach statistical significance, the median percentage change at 6 months in VAS scores was systematically higher in the treated group than in the placebo group, except for the knee. Moreover, at 6 months, a higher proportion of clinical responders, according to the VAS scores, were observed in the treated group for upper limbs (p<0.05), lumbar spine (p<0.05) and hip (p>0.05), compared to the placebo group.

TABLE 2

Proportion of clinical responders (%) at 6 months according to VAS by target joint.

| | Collagen hydrolysate | Placebo | p-Value |
|---|---|---|---|
| Shoulder, elbow, hand | n = 25 | n = 22 | |
| % Clinical responders | 60% | 27.3% | 0.024 |
| Lumbar spine | n = 24 | n = 36 | |
| % Clinical responders | 54.2% | 27.8% | 0.039 |
| Hip | n = 12 | n = 11 | |
| % Clinical responders | 66.7% | 45.5% | 0.305 |
| Knee | n = 32 | n = 27 | |
| % Clinical responders | 37.5% | 51.9% | 0.269 |

No statistically significant difference was observed between groups, neither concerning the utility value changes (p=0.54), nor for any of the dimensions of the SF-36 questionnaire (p between 0.33 and 0.98).

Most patients took a pain rescue treatment during their follow-up. In the collagen hydrolysate and placebo groups, 69.4% and 78.3% respectively of the patients reported to take at least one pain rescue treatment during the study. There was no statistically significant difference in either the median number of pills taken or in the median duration of treatment, between groups.

At 6 months, the satisfaction level in terms of efficacy was not statistically different in the two groups (Table 3). At each visit, a higher proportion of patients were moderately satisfied with their treatment. There was no statistically significant difference in terms of satisfaction about tolerability between groups, although there was some evidence that, in the majority of the patients, tolerability was judged in both groups as satisfactory or very satisfactory (Table 3).

TABLE 3

Proportion of patients (%) according to their level of satisfaction in terms of efficacy and tolerability.

| | Collagen hydrolysate | Placebo | p-Value |
|---|---|---|---|
| Satisfaction in terms of efficacy | | | |
| Very satisfied | 12.5% | 6.1% | |
| Satisfied | 20.8% | 25.5% | |
| Moderately satisfied | 31.3% | 30.6% | 0.433 |
| Dissatisfied | 27.1% | 24.5% | |
| Very dissatisfied | 8.3% | 13.3% | |
| Satisfaction in terms of tolerability | | | |
| Very satisfied | 43.3% | 40.4% | |
| Satisfied | 35.1% | 32.3% | |
| Moderately satisfied | 13.4% | 15.2% | 0.258 |
| Dissatisfied | 8.3% | 7.1% | |
| Very dissatisfied | 0% | 5.1% | |

There were no significant differences between groups in the number of subjects reporting at least one adverse event, in the incidence of serious adverse events, or in the incidence of adverse events considered to be possibly related to the study drug (Table 4).

TABLE 4

Proportion (%) of patients with at least one AE during the study, according to the AE class.

| | Collagen hydrolysate | Placebo | p-Value |
|---|---|---|---|
| Sense (eyes, ears, taste, olfaction) | 4.1% | 3.0% | 0.680 |
| Cardio-vascular | 3.1% | 8.1% | 0.129 |
| Respiratory | 15.5% | 22.2% | 0.227 |
| Gastro-intestinal | 15.5% | 26.3% | 0.063 |
| Hepatic/biliary | 0% | 0% | |
| Genito-urinary/reproduction | 5.2% | 1.0% | 0.092 |
| Kidney/renal | 0% | 0% | |
| Endocrine/metabolism | 2.1% | 3.0% | 0.667 |
| Musculo-skeletal | 23.7% | 16.2% | 0.186 |
| Hematology/lymphatic | 0% | 0% | |
| Neurological/psychiatric | 7.2% | 8.1% | 0.820 |
| Dermatological | 6.2% | 4.0% | 0.495 |
| Immunological | 1.0% | 0% | 0.311 |
| Allergy | 0% | 0% | |
| Others | 7.2% | 6.1% | 0.745 |

Discussion

In this 6-month randomized placebo controlled study, collagen hydrolysate was able to increase the proportion of clinical responders, as defined by an improvement of at least 20% in the VAS score, compared to patients receiving placebo, when this collagen hydrolysate is given for a 6-month period.

In this study, were included subjects with joint pain, whatever the localization and the diagnosis. Indeed, as an over-the-counter product, no diagnosis of any disease has to be performed. Consequently, in this study, are included subjects that are the targeted subjects of the product. Obviously, a substantial proportion of the study population has probably osteoarthritis, as in the general population.

In conclusion, in this 6-month randomized placebo controlled study, collagen hydrolysate is able to increase the proportion of clinical responders, as defined by an improvement of at least 20% in the VAS score, compared to patients receiving placebo.

Example 2—the Filipino Study

This study is intended to compare a treatment with a collagen hydrolysate versus the standard treatment of using analgesics for reduction of joint pain with less adverse effects. More particularly this study is focused on the effects of oral collagen hydrolysate treatment on the medial knee joint space and the functional outcome among patients diagnosed with osteoarthritis of the knee. (Bernado and Azarcon, 2012).

Specific Objectives
(a) To determine the effect of oral collagen treatment in improving the functional status of patients diagnosed with osteoarthritis of the knee using the Western Ontario and McMaster Universities (WOMAC) knee osteoarthritis index, Likert scale version.
(b) To determine the effect of oral collagen treatment in the knee joint space of patients diagnosed with osteoarthritis of the knee viewed and measured radiographically.
(c) To compare the effect of oral collagen treatment with the standard treatment using NSAID as to WOMAC knee osteoarthritis index and medial knee joint space.

Methodology
Study Design
Experimental, randomized, single blind observer, open-labeled, controlled trial.
Setting
Out-patient Department of a government hospital (Veterans Memorial Medical Center).
Selection of Subjects
One hundred and ten subjects were needed in this study to reject the null hypothesis that the response difference in the two groups is zero with a probability (power) of 0.8. Allowing for patient drop-outs, non-compliance to treatment and loss of test power due to non-parametric data analysis, a boosted sample of 75 patients per group was recommended.
Inclusion Criteria
Male and female patients aged 50-80 years old diagnosed with primary osteoarthritis of the knee defined by the American College of Rheumatology (ACR) criteria with Kellgren and Lawrence grade of at least 2 and above.
Medically stable (no fluctuating blood pressure, no active systemic infection).
Good cognitive function.
Willing to participate in the study.
Exclusion Criteria
Subjects who had taken any form of supplements or adjuvant therapy that may be indicated for the treatment of osteoarthritis like glucosamine sulfate, chondroitin sulfate, collagen, sodium hyaluronate, systemic or intra-articular corticosteroid therapy, and others that affect joint metabolism.
Subjects with secondary osteoarthritis (i.e. associated with obesity, inactivity, injury).
Obese patients [body mass index (BMI) greater than 27 calculated as weight in pounds divided by the square of height in inches times 703 or calculated as weight in kg divided by the square of height in meters].
Patients with active peptic ulcer disease or gastrointestinal bleeding.
Examination and Treatment Assignment
The patients recruited underwent the usual medical consultation from the Out-patient Department. The physician filled up a standardized history and physical examination form for each patient to determine the patient's eligibility in the study. All possible participants had an initial x-ray of the knee, anteroposterior view, in a weight bearing extended position to determine the Kellgren and Lawrence radiographic stage. Once eligible, the patient was invited to participate in the study and a written consent form was signed. Each subject was randomly assigned to Group A, which is the test group, or Group B, which is the control group. A list of random code that was auto-generated was given to qualified patients. They were assigned to the treatment groups corresponding to the given random code.

Group A subjects were given the oral collagen supplement (Genacol®, Blainville, Qc, Canada) 400 mg/capsule, 3 capsules daily at bedtime for 6 months, and a topical analgesic needed for knee pain. Group B, the control group, received the standard treatment using an oral non-steroidal inflammatory drug, in the form of aceclofenac 100 mg/tablet, 1 tablet twice a day for 5 days initially then as needed for pain, and topical analgesic (ketoprofen gel) to be applied twice a day as needed for pain. Both groups underwent physical therapy three times a week for two weeks. Heating modalities, range of motion exercises, and muscle strengthening exercises were administered on each therapy session.

Follow up evaluation was done every month. On the sixth month of follow up, repeat radiography evaluation of the involved knee was done to determine if there were any changes in the knee joint. Compliance to the study medication was determined by asking the patient on their missed doses and by counting the remaining unconsumed capsules.

Main Outcome Measurements

Symptoms of osteoarthritis were assessed using the Western Ontario and McMaster Universities (WOMAC) osteoarthritis index, a validated and disease-specific questionnaire separately addressing severity of joint pain (5 questions), stiffness (2 questions), and limitation of physical function (17 questions) in the 48 hours before assessment.

The Likert Version of WOMAC is rated on an ordinal scale of 0 to 4 with lower scores indicating lower levels of symptoms or physical disability. Each subscale is summated to a maximum score of 20, 8, and 68, respectively. There is also an index score or global score, which is most commonly calculated by summating the scores for the 3 subscales. The questionnaire is self administered and takes 5 to 10 minutes to complete.

The primary outcome measure for joint structural changes was represented by the mean joint space width of the medial compartment of the tibiofemoral joint. Weight bearing, anteroposterior radiographs of each knee were taken at baseline and at 6 months.

The patients stood bare-foot with their knees extended and their feet slightly internally rotated (~15°) and the posterior aspect of the knee in contact with the vertical cassette. The feet were positioned about 4 inches (about 10 cm) apart. The x-ray beam was centered about 1.5 inches (about 2.5 cm) inferior to the apex of the patella and perpendicular to the tibial plateau. The focus to film distance was approximately six feet. Using a standard ruler in millimeters, one experienced radiologist who was blinded as to the treatment of each subject measured the narrowest medial compartment of the tibiofemoral joint of each radiographed knee done at the start of the study. Measurement was repeated after the second x-ray done on the sixth month follow up. Results were compared and tabulated for analysis.

Statistical Analysis

Sample size was calculated on the basis of the recommendations available at the time of the study planning, of a 0.5 mm assumed difference in joint-space narrowing between the two groups. A sample size of at least 55 pairs of subjects was needed to be able to reject the null hypothesis that this response difference was zero with probability of (power) 0.8. The type I error probability associated with the test of this null hypothesis was 0.05. Allowing for patient drop outs, non-compliance to treatment and loss of test power due to non-parametric data analysis, a boosted sample of 75 patients per group was used.

Data was presented as mean±SD or frequency and percent distribution whichever was applicable. Chi square test was performed to indicate any significant difference in the distribution of male and female patients between the two groups while t-test was performed to check for any significant difference in characteristics that were continuous variables. Paired sample t-test was used to compare the significance in change in values (WOMAC and medial knee joint space) of the two groups from baseline to the sixth month follow up. A p-value of <0.050 was considered significant.

Results

Sample Baseline Characteristics

Of the 150 subjects enrolled and randomly assigned to the groups, 113 patients were able to finish the study. Thirty-seven of them were either lost to follow up or dropped out of the study. Fifty-five patients were in Group A while 58 patients were in Group B. Patients in Group A were mostly female (70.9%), with an average age of 68 years old. The average BMI was 24. Average baseline WOMAC Score was 3 (severe), average baseline Kellgren-Lawrence score was 3 (moderate) and average baseline median knee-joint space was 4 mm. Patients given drug B were also mostly female (67.2%), with average age of 69 years old. The average BMI was 24. Average baseline WOMAC Score was 3 (severe), average baseline Kellgren-Lawrence score was 3 (moderate) and average baseline median knee-joint space was 4 mm.

Table 5 shows that the baseline characteristics and demographics of both groups are homogenous. Table 6 shows that the average Global WOMAC Scores improved from baseline to each follow-up among patients from both groups.

TABLE 5

Baseline Characteristics: Distibution of Sex, Average Age, Height, Weight, BMI and Baseline scores

| Total No. of Patients | Group A 55 | | Group B 58 | | |
|---|---|---|---|---|---|
| | No | % | No. | % | p-value |
| Male | 16 | 29.1 | 19 | 32.8 | 0.48 |
| Female | 39 | 70.9 | 39 | 67.2 | |
| | Mean | SD | Mean | SD | |
| Age | 68 | 8.4 | 69 | 7.8 | 0.13 |
| Height (in) | 64 | 2.9 | 63 | 3.0 | 0.41 |
| Weight (lbs) | 139 | 18.6 | 138 | 14.5 | 0.33 |
| BMI | 24 | 2.0 | 24 | 1.5 | 0.49 |
| Baseline WOMAC Score | 3 | 0.7 | 3 | 0.7 | 0.47 |
| Baseline Kellgren-Lawrence Score | 3 | 0.7 | 3 | 0.7 | 0.48 |
| Baseline Median Knee-Joint Space (mm) | 4 | 2.2 | 4 | 1.7 | |

TABLE 6

WOMAC Scores from Baseline to Sixth Follow-up

| Total No. of Patients | Group A 55 | | Group B 58 | | |
|---|---|---|---|---|---|
| WOMAC Scores | Mean | SD | Mean | SD | p-value |
| Baseline | 2.83 | 0.7 | 2.91 | 0.7 | 0.47 |
| 1st ff-up | 2.38 | 0.6 | 2 59 | 0.7 | 0.42 |
| 2nd ff-up | 2.04 | 0.8 | 2.42 | 0.8 | 0.35 |
| 3rd ff-up | 1.65 | 0.7 | 2.29 | 0.8 | 0,25 |
| 4th ff-up | 1.30 | 0.8 | 2.26 | 0.9 | 0.16 |
| 5th ff-up | 1.05 | 0.9 | 2.17 | 0.9 | 0.14 |
| 6th ff-up | 0.76 | 0.9 | 1.87 | 1.2 | 0.11 |

No significant difference was found between the two groups in terms of average WOMAC Scores at each follow up.

Treatment Response

Figure 2:
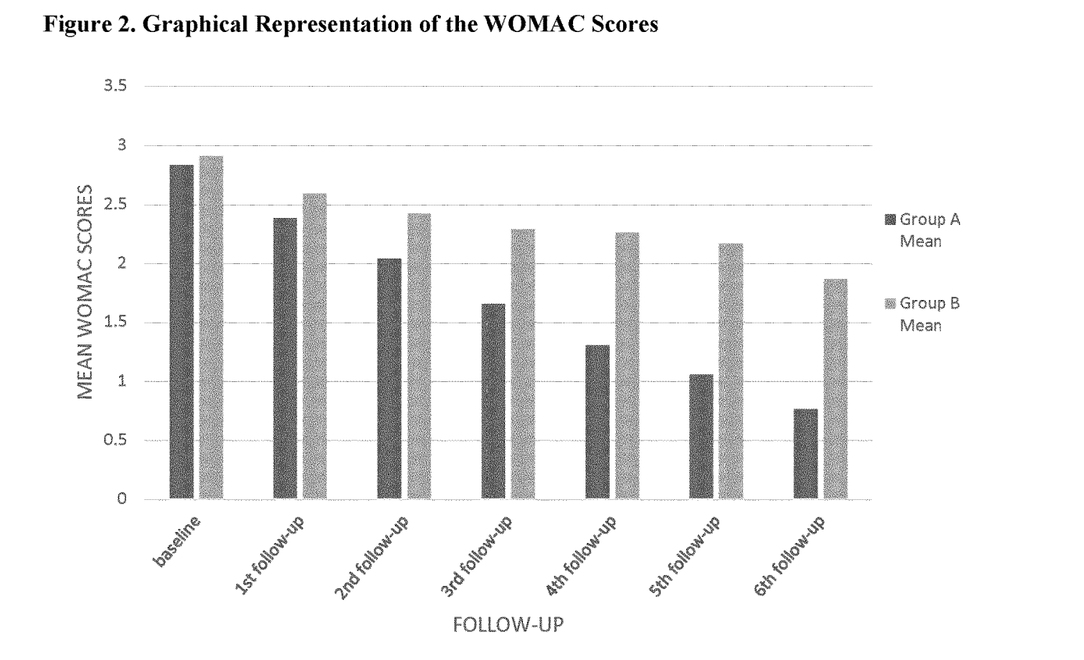
FIG. 2 shows a graphical representation of the WOMAC scores.

FIG. 2 shows the decreasing trend of the average WOMAC Scores of both groups; however, Group A had a lower WOMAC Score at the sixth follow as compared to Group B.

Table 7 shows that there was a significant drop in the average Global WOMAC Scores among patients in Group A from baseline to the sixth follow up compared with the other group where the drop in the WOMAC score was not statistically significant.

TABLE 7

Comparison of Global WOMAC Scores of Baseline to Sixth Follow-up

|  | Group A | | Group B | |
| --- | --- | --- | --- | --- |
|  | t-stat | p-value | t-stat | p-value |
| WOMAC 1st-Baseline | 0.5 | 0.33 | 0.3 | 0.37 |
| WOMAC 2nd-Baseline | 0.7 | 0.23 | 0.2 | 0.32 |
| WOMAC 3rd-Baseline | 1.1 | 0.13 | 0.1 | 0.29 |
| WOMAC 4th-Baseline | 1.4 | 0.08 | 0.1 | 0.29 |
| WOMAC 5th-Baseline | 1.5 | 0.07 | 0.1 | 0.26 |
| WOMAC 6th-Baseline | 1.8 | 0.04 | 0.0 | 0.21 |
| WOMAC 1st-Baseline | 0.5 | 0.33 | 0.3 | 0.37 |
| WOMAC 2nd-1st | 0.3 | 0.38 | 0.4 | 0.44 |
| WOMAC 3rd-2nd | 0.4 | 0.34 | 0.3 | 0.45 |
| WOMAC 4th-3rd | 0.3 | 0.37 | 0.4 | 0.49 |
| WOMAC 5th-4th | 0.2 | 0.41 | 0.4 | 0.46 |
| WOMAC 6th-5th | 0.3 | 0.38 | 0.4 | 0.40 |

Table 8 shows that among Group A patients, the average medial knee joint space widened from 4.2 mm at baseline to 4.4 mm at sixth follow up. On the other hand, the medial knee joint space among Group B patients narrowed from 4.3 mm to 3.8 mm. However, the difference was not statistically significant.

TABLE 8

Median Knee Joint Space at Baseline and Sixth Follow-up

| Total No. of Patients | Group A 55 | | Group B 58 | | |
| --- | --- | --- | --- | --- | --- |
|  | Mean | SD | Mean | SD | p-value |
| Median Knee Joint Space (mm) | | | | | |
| Baseline | 4.2 | 2.2 | 4.3 | 1.7 | 0.45 |
| 6th ff-up | 4.4 | 2.0 | 3.8 | 1.8 | 0.31 |
|  | p-value | | p-value | | |
| Knee Joint Space | | | | | |
| 6th - Baseline | 0.42 | | 0.32 | | |

Discussion

The clinical data collected in this study further confirms existing clinical data that show the positive influence of collagen hydrolysate on joint symptoms as well as improving the functional status in patients diagnosed with osteoarthritis. However, its effectiveness was more significant after six months of administration of the said medication as compared to that of the control group which showed no significant difference when comparing the baseline with the sixth follow up results. The longer time for this medication to take effect could be attributable to the smaller amount of dosage used in this study which was 1.2 grams of collagen hydrolysate daily, as compared to previous studies which used 10 grams daily and a significant difference in the joint symptoms was already seen at about six to eight weeks time. The clinical improvement in symptoms may be explained by the direct impact collagen hydrolysate has on the joint cartilage. It has the potential to rebuild some of the cartilage that may be lost during the osteoarthritic process by the stimulation of chondrocytes and the increased synthesis of extracellular matrix.

Structurally, this study did not show any significant change in the medial knee joint space of an osteoarthritic knee, however, there was note of increase in the average medial knee joint space between sixth follow up and baseline. Continuous administration of collagen hydrolysate for a longer period of time could possibly elicit a significant amount of improvement.

Conclusion

The administration of 1,200 milligrams of collagen hydrolysate of the invention daily for a period of six months has a beneficial impact on pain symptoms and joint function in patients with osteoarthritis. Significant improvement was seen in the WOMAC Score on the sixth month of intake of the said medication as compared to the intake of non-steroidal anti-inflammatory drugs. Structurally, however, there was no statistically significant improvement in the medial knee joint space of patients with osteoarthritis after six months in the intake of either medication.

Example 3—the Second Filipino Study

Adults older than 50 years suffering from keen pain were enrolled in a triple-blind placebo-controlled randomized controlled trial to study the effect of standard home exercise program combined with a treatment with capsules of the collagen hydrolysate (Molecular weight of 1000 Daltons or less; 1200 mg/day) of the invention for 6 months. The control group took placebo. There was a significant improvement in the cartilage thickness, clarity and abrasion grade as well as a significant reduction in lateral meniscus protrusion in the treated group and an increase in exercise compliance. The study was completed in January 2016.

Methodology

Research Design:

Triple-blind placebo-controlled randomized controlled trial

Setting of the Sample:

Adults of more than 50 years old, any gender, occupation and educational attainment, with complaint of knee pain of at least one month duration and residing in Metro Manila, Philippines, from January 2013-June 2015

Participant Screening and Recruitment

Participants were screened through preliminary medical history review and physical examination. Inclusion criteria were based on the Altman's criteria for classification of idiopathic osteoarthritis of the knee (see Table 9). Exclusion criteria are shown on Table 10.

TABLE 9

Altman's Criteria for Classification of Idiopathic Osteoarthritis of the Knee

| Clinical and Laboratory* | Clinical and Radiographic | Clinical† |
| --- | --- | --- |
| Knee pain + at least 5 of 9: Age > 50 years | Knee pain + at least 1 of 3: Age > 50 years | Knee pain + at least 3 of 6: Age > 50 years |

TABLE 9-continued

Altman's Criteria for Classification
of Idiopathic Osteoarthritis of the Knee

| Clinical and Laboratory* | Clinical and Radiographic | Clinical† |
|---|---|---|
| Stiffness < 30 minutes | Stiffness < 30 minutes | Stiffness < 30 minutes |
| Crepitus | Crepitus + | Crepitus |
| Bony tenderness | Osteophytes | Bony tenderness |
| Bony enlargement | (radiographic) | Bony enlargement |
| No palpable warmth | | No palpable warmth |
| ESR < 40 mm/hr | | |
| RF < 1:40 | | |
| SF OA | | |
| 92% sensitive | 91% sensitive | 95% sensitive |
| 75% specific | 86% specific | 69% specific |

*ESR = erythrocyte sedimentation rate (Westergren); RF = rheumatoid factor; SF OA = synovial fluid signs of OA (clear, viscous or white blood cell count <2,000/mm$^3$)
†Alternative for the clinical category would be 4 of 6, which is 84% sensitive and 89 % specific.

TABLE 10

Exclusion criteria for participants

| Medical History | Procedures | Objective Findings |
|---|---|---|
| Previous intake of collagen hydrolysate or any form of supplement in the past week | Intra-articular injection of hyaluronic acid (past 6 months) or corticosteroids (past month) | Limited knee range of motion which would prevent proper positioning |
| Known hypersensitivity/ allergy to collagen Hydrolysate | Previous arthroscopy or surgery of the knee | Severe genu varus or valgus deformity |
| Presence of other arthropathy i.e. rheumatoid arthritis, gouty arthritis, septic arthritis | | Minimal or absent knee joint space on x-ray |

Sample Size Calculation

Based on the study of Bruyere et al. in 2012 and using the statistical software Stata 11, a sample size of 50 participants per treatment arm or a total of 100 was necessary to achieve an 80% power of the study at an alpha level of 0.05. We decided to add at least 10% more participants to compensate for possible drop-outs during the conduct of the study.

Methods

Participants included in the study were allocated into an intervention group or a control group. Both groups were instructed with a standard home exercise program for knee osteoarthritis which has been validated by Mercado et al. in 2012. Members of the intervention group were asked to take 3 capsules of collagen hydrolysate 400 mg/capsule (Brand name: Genacol) daily for six months while the control group took placebo. Each participant was also instructed to keep a daily journal/diary for documentation of the occurrence of knee pain, performed exercises, and intake of additional medications during the study.

Standard Treatment for Knee OA

Standard treatment for both groups included instructions on proper effective exercises for knee OA. The exercise program was composed of strengthening exercises for the hip and knee musculature, stretching exercises and walking as a form of aerobic exercise. These exercises were to be done at least twice a week for six months. Paracetamol 500 mg-tablets were also provided as rescue medications for episodes of severe pain warranting intake of medication.

Study Medications

The medications contained 400 mg of collagen hydrolysate for the intervention group and an equal amount of maltodextrin as placebo for the control group.

Criteria for Study Termination or Participant Withdrawal

The following criteria for termination of the study or subject participation were used:
 1. Participant's voluntary refusal
 2. Increasing knee pain even with intake of NSAID or other medications
 3. Presence of adverse events related to intake of the study medications (i.e. fever, eructation, severe gastrointestinal disorder, allergic reaction) or other unrelated medical conditions that would prevent further participation Outcome Measures Pain Visual Analogue Scale (VAS): The Pain VAS used in this study is a graphic rating scale format composed of a horizontal line 100 mm in length, divided equally with 6 vertical lines to produce a 0-10 scale (with intervals of 2) and anchored by word descriptors and different faces at each line. The participant marks the point that represents their current state of pain. The VAS score is measured in millimeters from the left hand end of the line to the point that the participant marks. It has an excellent test-retest reliability (r=0.94) and moderate to good construct validity (r=0.62-0.91) compared with similar pain rating scales. *The Western Ontario and McMaster Universities Osteoarthritis Index (WOMAC)*: The WOMAC is a self-administered questionnaire used to assess pain, stiffness and physical function among patients with hip and/or knee OA. It is composed of 24 items divided into the subscales of pain (5 items), stiffness (2 items) and physical function (17 items). This study used the 100-mm VAS format Tagalog version with anchors of *hindi masakit/walang paninigas/hindi mahirap and masakit na masakit/matinding paninigas/napakahirap.* The participant marks the point on the line that represents their current symptom with regarding the context described by the items. The item score is determined by measuring in millimeters from the left hand end of the line to the point that the participant marks. Possible score ranges per subscale area as follows: pain=0-500, stiffness=0-200, physical function=0-1700. The total WOMAC score is the sum of the scores for all of the items (max score=2400) with higher scores indicating worse pain, stiffness and functional limitations. Its psychometric properties showed acceptable to excellent internal consistency and test-retest reliability (Cronbach alpha 0.70-0.91; ICC 0.58-0.92) and moderate to high construct validity correlations with other similar instruments (American College of Rheumatology, 2015).

Sonographic Measurements of the Knee Cartilage and Soft Tissue Structures

The musculoskeletal ultrasound protocol for knee osteoarthritis developed by Bernardo et al. in 2014 was adopted for the sonographic assessments in this study (see FIG. 3). The following structures were scanned, and the subsequent parameters were measured thrice according to the protocol:

1. Articular cartilage (medial and lateral femoral condylar area)
   a. Narrowest anteroposterior diameter of the articular cartilage (in centimeters)
   b. Cartilage clarity—how well the cartilage borders could be distinguished from the overlying intra-articular soft tissues and scored as follows: 1—excellent; 2—good; 3—poor; and 4—worst.
   c. Cartilage grade—the severity of focal cartilaginous lesions and scored as follows:
      0—normal; 1—minimal abrasion; 2—partial defect; 3—defect extending down to intact subchondral bone; and 4—defect involving the subchondral bone.
2. Suprapatellar and infrapatellar recess
   a. Largest anteroposterior diameter of effusion (in centimeters)
   b. Degree of synovitis
      Thickness of the synovial tissue was graded as follows: normal—no synovitis; mild—flat, thickened synovium; moderate—thickened synovium with few villi-like protrusions; severe—marked thickening with multiple villi-like protrusions.
   c. Power Doppler Signal (PDS)
   Blood flow in the synovial membrane was evaluated using the power Doppler signal and graded as follows: 1—normal or minimal tissue perfusion, 2—mild hyperemia, 3—moderate hyperemia, and 4—marked hyperemia.
3. Medial and lateral menisci
   a. Meniscal protrusion
      A line is drawn from the femur to the tibia and the height of a perpendicular line drawn from this line to the highest point of the meniscus is measured in centimeters
      4. Pes anserine bursitis
   a. Widest antero-posterior diameter of bursitis (in centimeters)
   b. Power Doppler Signal
5. Posterior knee (Baker's cyst)
   a. Widest transverse diameter of the cyst (in centimeters)
   Other findings noted during the scans were also noted such as the presence of osteophytes, tendinopathies, panniculitis and meniscal breaks.

Data Collection

All participants were assessed at baseline and after 6 months. In each assessment, the following procedures were conducted: medical history taking, physical examination, completion of WOMAC and ultrasonography of both knees.

Medical History and Physical Examination

Participants filled out a data sheet which obtained the following data: name, age, gender, address, occupation, contact information, comorbid diseases, previous surgeries, current medications and treatments. Data pertinent to OA were also obtained: affected knee, worst pain score on the affected knee rated using pain VAS, number of years diagnosed with OA (if previously diagnosed through x-ray or consultation), exercise compliance and medications taken for pain.

The following physical parameters were subsequently assessed: range of motion of both knees, knee deformity (genu valgus/varus), swelling and/or warmth, height and weight.

Sonography of the Knee

Gray scale ultrasound using Sonosite M-Turbo ultrasound machines (Washington, USA) with linear transducers (bandwidth 13-6 MHz, scan depth 6 cm) and Power Doppler capabilities were used. Five certified sonologists (one orthopedic surgeon, one rheumatologist, three physiatrists) who were part of the musculoskeletal ultrasound protocol development team performed the procedure on the participants. They were blinded to participant allocation.

Treatment of Data

Prior to the statistical analysis, the measurement of the femoro-tibial cartilage thickness and grading of cartilage quality using the two methods (longitudinal and transverse views) were correlated and showed significant correlation. Thus, the investigators decided to use the cartilage measurements in the trochlear region obtained through the transverse view which provided articular cartilage thickness measurements of the central region. Exercise compliance, on the other hand, was interpreted as performance of the standard exercise regimen at least twice a week during the period of the study.

Statistical Analysis

Means and standard deviations were computed for the demographic data, VAS pain score, WOMAC overall and subscale scores and sonographic measurements. Mann-Whitney, Fisher's Exact and McNemar's Change tests were used when applicable to detect significant differences between treatment groups for categorical and continuous variables. Subgroup analysis was performed on the participants who did not regularly exercise to determine the effect of collagen hydrolysate on VAS pain score, WOMAC overall and subscale scores and sonographic measurements Intention-to-treat analysis was performed. A p value of <0.05 was considered significant for all of the statistical tests.

Results

Participant Characteristics

TABLE 11

Baseline characteristics of study participants

|  | Total | Intervention Group | Control Group | p value |
|---|---|---|---|---|
| No. of participants | 109 | 56 | 53 |  |
| Males/Females | 23/86 | 13/43 | 10/43 | 0.64 |
| Age in years, mean (SD) | 64.1 (8.3) | 64.1 (8.6) | 62.7 (10.2) | 0.96 |
| Weight in kg, mean (SD) | 62.2 (7.0) | 61.6 (10.4) | 62.7 (10.2) | 0.42 |
| Height in cm, mean (SD) | 152.5 (7.1) | 152.7 (7.4) | 152.7 (9.0) | 0.60 |
| Body mass index in kg/m$^2$, mean (SD) | 26.8 (2.9) | 26.4 (3.9) | 27.0 (4.8) | 0.84 |
| Knee involvement (unilateral/bilateral) | 3/106 | 1/55 | 2/51 | 0.61 |

TABLE 11-continued

Baseline characteristics of study participants

|  | Total | Intervention Group | Control Group | p value |
|---|---|---|---|---|
| Pain VAS score, mean (SD) | 4.6 (3.1) | 4.6 (3.0) | 4.6 (2.9) | 1.00 |
| WOMAC Overall Score, mean (SD) | 790.0 (520.6) | 795.4 (545.2) | 752.2 (490.4) | 0.75 |
| Exercise compliance (compliant/non-compliant) | 10/99 | 3/53 | 7/46 | 0.20 |

A total of 109 participants were included in the study and randomly allocated to treatment groups. The number of participants who withdrew from the study was similar: 44 completed the program in the intervention group and 43 completed the program in the placebo group. Majority of the participants were females, had bilateral knee pain and were non-compliant to exercise recommendations before intervention. Height, weight, body mass index, pain VAS and WOMAC scores were similar for both treatment groups with no significant differences (see Table 11).

Pain VAS Score, WOMAC Score and Exercise Compliance

TABLE 12

Baseline and post-intervention overall WOMAC scores, pain VAS scores and exercise compliance count

|  | Intervention Group (n = 56) | Control Group (n = 53) | p value |
|---|---|---|---|
| Overall WOMAC Score [mean, (SD)] |  |  |  |
| Pre-intervention | 795.4 (545.2) | 752.2 (490.4) | 0.75 |
| Post-intervention | 596.4 (549.8) | 537.5 (400) | 0.99 |
| Mean change | −16.1 (41.5) | −21.5 (60.4) | 0.46 |
| Pain VAS score [mean, (SD)] |  |  |  |
| Pre-intervention | 4.6 (3.0) | 4.6 (2.9) | 1.00 |
| Post-intervention | 2.2 (2.6) | 2.2 (2.9) | 0.66 |
| Mean change | −2.4 (2.9) | −2.4 (3.3) | 0.75 |
| Exercise Compliance (Compliant/Non-compliant) |  |  |  |
| Pre-intervention | 3/53 | 7/46 | 0.20 |
| Post intervention | 35/21 | 39/14 | 0.23 |
| P value | 0.000[a] | 0.000[a] |  |

[a]Significant

Overall WOMAC and pain VAS scores decreased compared to baseline in both treatment groups. However, there was no statistically significant difference between the two groups for these two outcome measures. However, there was a significant increase in exercise compliance by 62.5% in the intervention group and 73.5% in the control group (see Table 12).

Sonographic Measurements and Findings

There were minimal though statistically significant differences between the baseline values of the two treatment groups with regard to medial meniscus protrusion and deep infrapatellar bursitis measurements. The rest of the baseline values for femoro-tibial articular cartilage thickness and characteristics as well other soft tissue findings were similar and not statistically different for both groups (see Tables 13-18).

Cartilage Thickness, Clarity and Abrasion

TABLE 13

Baseline and post-intervention sonographic measurements of femoro-tibial articular cartilage thickness (in centimeters)

|  | Intervention Group (n = 56) | Control Group (n = 53) | p value |
|---|---|---|---|
| Medial Cartilage [mean, (SD)] |  |  |  |
| Pre-intervention | 0.11 (0.05) | 0.11 (0.06) | 0.52 |
| Post-intervention | 0.14 (0.05) | 0.14 (0.05) | 0.61 |
| Mean change | 0.03 (0.04) | 0.03 (0.05) | 0.56 |
| Central Cartilage [mean, (SD)] |  |  |  |
| Pre-intervention | 0.14 (0.04) | 0.15 (0.05) | 0.47 |
| Post-intervention | 0.16 (0.04) | 0.16 (0.05) | 0.80 |
| Mean change | 0.02 (0.04) | 0.01 (0.04) | 0.27 |
| Lateral Cartilage [mean, (SD)] |  |  |  |
| Pre-intervention | 0.14 (0.11) | 0.12 (0.04) | 0.52 |
| Post-intervention | 0.15 (0.08) | 0.14 (0.04) | 0.54 |
| Mean change | 0.01 (0.08) | 0.02 (0.04) | 0.51 |

TABLE 14

Baseline and post-intervention sonographic assessment of femoro-tibial articular cartilage characteristics

|  | Intervention Group (n = 56) | Control Group (n = 53) | p value |
|---|---|---|---|
| Clarity |  |  |  |
| Medial Cartilage [mean, (SD)] |  |  |  |
| Pre-intervention | 2.85 (0.56) | 2.91 (0.59) | 0.41 |
| Post-intervention | 2.59 (0.74) | 2.61 (0.72) | 0.66 |
| Mean change | −0.26 (0.87) | −0.29 (0.79) | 0.93 |
| Central Cartilage [mean, (SD)] |  |  |  |
| Pre-intervention | 2.79 (0.62) | 2.86 (0.62) | 0.39 |
| Post-intervention | 2.39 (0.75) | 2.51 (0.71) | 0.17 |
| Mean change | −0.40 (0.86) | −0.35 (0.79) | 0.54 |
| Lateral Cartilage [mean, (SD)] |  |  |  |
| Pre-intervention | 2.82 (0.54) | 2.86 (0.52) | 0.50 |
| Post-intervention | 2.36 (0.68) | 2.42 (0.63) | 0.45 |
| Mean change | −0.46 (0.83) | −0.43 (0.78) | 0.64 |

TABLE 14-continued

Baseline and post-intervention sonographic assessment
of femoro-tibial articular cartilage characteristics

|  | Intervention Group (n = 56) | Control Group (n = 53) | p value |
|---|---|---|---|
| Abrasion | | | |
| Medial Cartilage [mean, (SD)] | | | |
| Pre-intervention | 2.22 (1.29) | 1.99 (1.39) | 0.19 |
| Post-intervention | 2.10 (1.07) | 2.37 (1.30) | 0.07 |
| Mean change | −0.13 (1.22) | 0.38 (1.31) | 0.009[b] |
| Central Cartilage [mean, (SD)] | | | |
| Pre-intervention | 1.33 (1.29) | 1.52 (1.27) | 0.06 |
| Post-intervention | 1.77 (0.95) | 1.82 (1.06) | 0.64 |
| Mean change | −0.06 (1.25) | 0.30 (1.10) | 0.013[b] |
| Lateral Cartilage [mean, (SD)] | | | |
| Pre-intervention | 1.83 (1.31) | 1.57 (1.30) | 0.12 |
| Post-intervention | 1.83 (0.80) | 1.83 (1.10) | 0.71 |
| Mean change | 0 (1.27) | 0.26 (1.27) | 0.16 |

[b]Significant

After the intervention, there was a significant mean change of cartilage abrasion grading of the medial (−0.13±1.22, p=0.009) and central (−0.6±1.25, p=0.013) portions of the articular cartilage in the trochlear area for the intervention group. The cartilage thickness and clarity of the articular cartilage was not significantly different between the two groups (see Tables 13-14).

Periarticular Soft Tissue Changes

TABLE 15

Baseline and post-intervention sonographic measurement
of meniscal protrusion in centimeters [mean, (SD)]

|  | Intervention Group (n = 56) | Control Group (n = 53) | p value |
|---|---|---|---|
| Medial meniscus | | | |
| Pre-intervention | 0.20 (0.19) | 0.26 (0.19) | 0.02[b] |
| Post-intervention | 0.20 (0.23) | 0.25 (0.23) | 0.06 |
| Mean change | 0.00 (0.20) | −0.01 (0.18) | 0.94 |
| Lateral meniscus | | | |
| Pre-intervention | 0.20 (0.16) | 0.23 (0.17) | 0.08 |
| Post-intervention | 0.13 (0.16) | 0.18 (0.21) | 0.05[b] |
| Mean change | −0.08 (0.16) | −0.05 (0.19) | 0.22 |

[b]Significant

TABLE 16

Baseline and post-intervention sonographic
assessment of the suprapatellar recess

|  | Intervention Group (n = 56) | Control Group (n = 53) | p value |
|---|---|---|---|
| Synovitis (with/without) | | | |
| Pre-intervention | 58/54 | 69/37 | 0.16 |
| Post-intervention | 58/54 | 66/40 | 0.20 |
| Suprapatellar bursitis Anteroposterior diameter, in centimeters [mean, (SD)] | | | |
| Pre-intervention | 0.23 (0.29) | 0.30 (0.36) | 0.17 |
| Post-intervention | 0.14 (0.26) | 0.19 (0.32) | 0.40 |
| Mean change | −0.09 (0.29) | −0.11 (0.37) | 0.41 |

TABLE 17

Baseline and post-intervention sonographic
assessment of the infrapatellar recess

|  | Intervention Group (n = 56) | Control Group (n = 53) | p value |
|---|---|---|---|
| Infrapatellar panniculitis (with/without) | | | |
| Pre-intervention | 6/106 | 3/103 | 0.50 |
| Post-intervention | 32/80 | 42/64 | 0.09 |
| Bursitis Anteroposterior diameter, in centimeters [mean, (SD)] | | | |
| Superficial infrapatellar area | | | |
| Pre-intervention | 0.00 (0.02) | 0.01 (0.10) | 0.94 |
| Post-intervention | 0.00 (0.02) | 0.00 (0.00) | 0.33 |
| Mean change | 0.0 (0) | −0.01 (0.10) | 0.52 |
| Deep infrapatellar area | | | |
| Pre-intervention | 0.03 (0.11) | 0.00 (0.02) | 0.014[b] |
| Post-intervention | 0.01 (0.07) | 0.00 (0.00) | 0.09 |
| Mean change | −0.02 (0.09) | 0.0 (0.02) | 0.07 |

[b]Significant

TABLE 18

Baseline and post-intervention sonographic assessment
of other periarticular soft tissue findings

|  | Intervention Group (n = 56) | Control Group (n = 53) | p value |
|---|---|---|---|
| Pes anserine bursitis Anteroposterior diameter in centimeters [mean, (SD)] | | | |
| Pre-intervention | 0.02 (0.07) | 0.03 (0.13) | 0.87 |
| Post-intervention | 0.01 (0.04) | 0.00 (0.02) | 0.06 |
| Mean change | 0 (0.07) | −0.03 (0.13) | 0.11 |
| Popliteal (Baker's) cyst Transverse diameter in centimeters [mean, (SD)] | | | |
| Pre-intervention | 0.23 (0.59) | 0.34 (0.82) | 0.25 |
| Post-intervention | 0.18 (0.59) | 0.30 (0.84) | 0.20 |
| Mean change | −0.05 (0.36) | −0.05 (0.32) | 0.55 |

There was a significant difference between the two groups post-intervention with regard to lateral meniscus protrusion. The intervention group showed a notable reduction (from 0.20±0.16 cm to 0.13±0.16 cm) compared to the control group (from 0.23±0.17 cm to 0.18±0.21 cm). There was no significant difference between the treatment groups for the other soft tissue findings (see Tables 15-18).

Subgroup Analysis of Participants Who were Non-Compliant with Regular Exercise.

There were 21 and 14 participants in the intervention and control groups that were non-compliant with performing regular exercise. The pre-intervention VAS score was not statistically different with the two groups. However, during post-intervention, there was a significantly lower VAS score for the intervention group as compared to the control group (3.0±2.9 vs 5.1±3.0; p value 0.03). There was no statistical difference with the WOMAC score of both groups.

TABLE 19

VAS score of experimental and control groups who were non-compliant to regular exercise

|  | Intervention Group (n = 21) | Control Group (n = 14) | p value |
|---|---|---|---|
| Overall WOMAC Score [mean, (SD)] | | | |
| Pre-intervention | 805.3 (569.4) | 686.2 (528.1) | 0.55 |
| Post-intervention | 646.5 (519.1) | 627.8 (403.5) | 0.74 |
| Mean change | −16.7 (27.4) | −3.2 (10.6) | 0.23 |
| Pain VAS score [mean, (SD)] | | | |
| Pre-intervention | 3.7 (2.7) | 5.6 (3.0) | 0.09 |
| Post-intervention | 3.0 (2.9) | 5.1 (3.0) | 0.03[a] |
| Mean change | −0.8 (1.9) | −0.5 (1.4) | 0.54 |

[a]Significant

Sonographic Measurements and Findings

There was no statistical difference with the cartilage thickness, clarity and abrasion of the intervention and control group at baseline. After six months, the intervention group had a thicker cartilage measurement in the central portion (0.15±0.04 cm vs 0.12±0.04 cm, p value=0.03) (Table 20). The intervention group demonstrated significant improvements in the post-intervention cartilage clarity at the central and lateral area as compared with the control group (central area: 2.55±0.71 vs 2.82±0.7; p value=0.05; lateral area: 2.47±0.67 vs 2.82±0.6; p value=0.01). There was also a significant mean difference in the clarity score of the lateral cartilage in the intervention group (−0.28±0.55 vs −0.07±0.60) with a p value of 0.03 (Table 21).

There was no statistical difference between intervention and control groups in the cartilage abrasion scores and peri-articular soft tissue findings at baseline and post-intervention.

TABLE 20

Baseline and post-intervention sonographic measurements of femoro-tibial articular cartilage thickness (in centimeters)

|  | Intervention Group (n = 21) | Control Group (n = 14) | p value |
|---|---|---|---|
| Medial Cartilage [mean, (SD)] | | | |
| Pre-intervention | 0.11 (0.05) | 0.11 (0.08) | 0.48 |
| Post-intervention | 0.12 (0.05) | 0.11 (0.08) | 0.25 |
| Mean change | 0.003 (0.03) | −0.003 (0.02) | 0.56 |
| Central Cartilage [mean, (SD)] | | | |
| Pre-intervention | 0.15 (0.04) | 0.13 (0.04) | 0.06 |
| Post-intervention | 0.15 (0.04) | 0.12 (0.04) | 0.03[a] |
| Mean change | 0.002 (0.02) | −0.001 (0.02) | 0.27 |
| Lateral Cartilage [mean, (SD)] | | | |
| Pre-intervention | 0.15 (0.13) | 0.12 (0.03) | 0.15 |
| Post-intervention | 0.15 (0.13) | 0.11 (0.03) | 0.54 |
| Mean change | 0.004 (0.02) | 0.0004 (0.003) | 0.50 |

[a]significant

TABLE 21

Baseline and post-intervention sonographic assessment of femoro-tibial articular cartilage characteristics

|  | Intervention Group (n = 21) | Control Group (n = 14) | p value |
|---|---|---|---|
| Clarity | | | |
| Medial Cartilage [mean, (SD)] | | | |
| Pre-intervention | 2.90 (0.53) | 2.93 (0.54) | 0.85 |
| Post-intervention | 2.66 (0.69) | 2.82 (0.72) | 0.66 |
| Mean change | −0.23 (0.73) | −0.10 (0.57) | 0.93 |
| Central Cartilage [mean, (SD)] | | | |
| Pre-intervention | 2.7 (0.65) | 2.86 (0.52) | 0.39 |
| Post-intervention | 2.55 (0.71) | 2.82 (0.7) | 0.05[a] |
| Mean change | −0.21 (0.60) | −0.03 (0.51) | 0.15 |
| Lateral Cartilage [mean, (SD)] | | | |
| Pre-intervention | 2.76 (0.53) | 2.89 (0.42) | 0.24 |
| Post-intervention | 2.47 (0.67) | 2.82 (0.6) | 0.01[a] |
| Mean change | −0.28 (0.55) | −0.07 (0.60) | 0.03[a] |
| Abrasion | | | |
| Medial Cartilage [mean, (SD)] | | | |
| Pre-intervention | 1.92 (1.35) | 1.93 (1.84) | 0.91 |
| Post-intervention | 1.95 (1.24) | 1.78 (1.81) | 0.49 |
| Mean change | 0.02 (0.56) | −0.14 (0.59) | 0.27 |
| Central Cartilage [mean, (SD)] | | | |
| Pre-intervention | 1.50 (1.21) | 1.21 (1.37) | 0.26 |
| Post-intervention | 1.50 (1.06) | 1.10 (1.31) | 0.09 |
| Mean change | 0.00 (0.69) | −0.10 (1.10) | 0.45 |
| Lateral Cartilage [mean, (SD)] | | | |
| Pre-intervention | 1.69 (1.35) | 1.39 (1.42) | 0.36 |
| Post-intervention | 1.71 (1.15) | 1.36 (1.44) | 0.18 |
| Mean change | 0.02 (0.84) | −0.03 (0.33) | 0.56 |

[a]significant

Adverse Events

Two participants from the intervention group and one participant from the control group experienced a feeling of bloatedness after two to three days of taking their assigned medications. They were advised to discontinue their medication for one week. Upon resumption of medication intake, no recurrence of previous symptoms was noted for all three patients. One participant from the intervention group experienced a hypersensitivity skin reaction after the second day of taking his assigned medication. This participant was given appropriate medical management and was advised to terminate his participation from the study. The manufacturer was also informed of this adverse reaction.

Discussion

This study, to our knowledge, is the first to determine the effect of collagen hydrolysate in combination with a standard treatment for knee osteoarthritis (i.e. exercise) on pain score, functional status, articular cartilage characteristics and soft tissue changes using sonography.

Pain and WOMAC scores in both of our treatment groups improved but did not reach statistical significance. The studies of Moskowitz (2000) and McAlindon et al. (2011) also showed similar results. One plausible explanation for this result is that the participants in both groups probably had milder OA symptoms as demonstrated by their baseline mean pain VAS and WOMAC scores not exceeding 50% of the highest possible score. Moskowitz and McAlindon et al. mentioned that variability in clinical severity at the onset may affect the expected magnitude of change as patients with more severe symptoms have a greater potential for improvement. On the other hand, the incongruity of our findings with that of Benito-Ruiz et al. (2009) and Bernardo and Azarcon (2012) may be attributed to the difference in our standard treatments. Utilization of a 6-month exercise program as our standard treatment, in accordance to the general consensus for OA (Trojian et al., 2016), translated into an increase in exercise compliance and expected manifestation of its benefits among the participants from both treatment groups in terms of improved function and well-being. This may very well explain the observed improvement in pain and WOMAC scores of our participants. However, with a subgroup analysis of participants who were not compliant to exercise showed similar results to the study of Benito-Ruiz et al (2009) and Bernardo and Azarcon (2012) which showed that collagen hydrolysate could significantly decrease pain in knee osteoarthritis.

Several investigators have studied different dietary supplements and interventions to identify the best approach that can delay the structural progression of OA (Gregory and Fenner, 2014). Our study on collagen hydrolysate may be the first to document structural modifications in osteoarthritic knees. We have found significant improvement in the cartilage thickness, clarity and abrasion grade as well as a significant reduction in lateral meniscus protrusion in our intervention group. These changes pose relevant implications for the management of OA.

Previous studies on collagen hydrolysate have found that it preferentially accumulates in cartilage and stimulates chondrocyte metabolism and collagen synthesis. This, in theory, will strengthen the cartilage and possibly delay the progression of OA. Other studies, on the other hand, have emphasized the significant association between the severity of meniscal tears and extrusions and the progression of cartilage volume loss. The menisci provide some protection to cartilage when they are positioned properly within the knee. However, due to numerous mechanical and biological factors, the meniscus may protrude and lose articulation with the cartilage which may then contribute to degeneration. Exercise may then play a role in strengthening the structures surrounding the knee to provide external support. In light of these information, it may be probable that the combination of exercise and collagen hydrolysate intake can promote structural modification and delay the progression of cartilage loss in normal and osteoarthritic knees.

A possible limitation of our study is the duration of intervention. Although most of the previous studies on collagen were conducted between three to six months, it may be prudent to extend the follow-up period to be able to observe more prominent changes in the outcome measures as there has been no established onset of effect for collagen hydrolysate as of date. A case report which studied the effect of intraarticular injection of platelet-rich plasma (PRP) in patients with knee osteoarthritis also supports this recommendation because no change in the articular cartilage using MRI was observed until one year after the injection of PRP. Other recommendations for future studies may include balancing of participants in terms of occupation and OA severity and recruitment of a larger sample size.

Conclusion

Our study showed that collagen hydrolysate in addition to exercise decreased pain, improved overall functional status and produced intraarticular and periarticular structural modifications (i.e. improvement of cartilage abrasion grade and reduction of lateral meniscal protrusion) in patients with knee osteoarthritis.

In the subgroup analysis of participants who were not compliant with the regular exercise, intake of collagen hydrolysate could significantly lower pain VAS score with improvement in the structure of the articular cartilage with regards to its thickness and clarity.

The present description refers to a number of documents, the content of which is herein incorporated by reference in their entirety.

The scope of the claims should not be limited by the preferred embodiments set forth in the examples, but should be given the broadest interpretation consistent with the description as a whole. When a range of values is described, the person of ordinary skill in the art would understand that all values within this range are included, also not specifically listed.

REFERENCES

1. Bruyère O, et al. Effect of collagen hydrolysate in articular pain: A 6-month randomized, double-blind, placebo controlled study. Complement Ther Med (2012), doi: 10.1016/j.ctim.2011.12.007
2. Schrieber et al. The role of collagen hydrolysate in the prophylaxis of osteoarthritis and osteoporosis, in Gelatin handbook, Wiley ed, 2007 pp. 301-309
3. EP 1 885 771, CA 2 854 856, U.S. Pat. No. 9,072,724, WO 2013/079373
4. Bernado and Azarcon, PARM proceedings, 2012, vol 4, issue 1, pages 1-8
5. Suarez et al., Effect of collagen hydrolysate as adjuvant treatment to exercise for knee osteoarthritis, PARM Proceedings, 2017, vol. 9, issue 1, pages 4-15.
6. Clark K L, Sebastianelli W, Flechsenhar K R, Aukermann D F, Meza F, Millard R L, et al. 24-Week study on the use of col-lagen hydrolysate as a dietary supplement in athletes with activity-related joint pain. Curr Med Res Opin 2008; 24 May (5)):1485-96.
7. Moskowitz R W. Role of collagen hydrolysate in bone and joint disease. Sem in Arthritis Rheum 2000; 30 (October (2)):87-99.
8. McAlindon, T E., Nuite, M., Krishnan, N., Ruthazer, R., Price, L L., Burstein, D. et al. (2011). Change in knee osteoarthritis cartilage detected by delayed gadolinium enhanced magnetic resonance imaging following treatment with collagen hydrolysate: A pilot randomized controlled trial. *Osteoarthritis and Cartilage,* 19, 399-405. doi:10.1016/j.joca.2011.01.001
9. Benito-Ruiz, P., Camacho-Zambrano, M M., Carrillo-Arcentales, J N., Mestanza-Peralta, M A., Vallejo-Flores, C A., Vargas-Lopez, S V. et al. (2009). A randomized controlled trial on the efficacy and safety of a food ingredient, collagen hydrolysate, for improving joint comfort. *International Journal of Food Sciences and Nutrition,* 60 (S2), 99-113. doi: 10.1080/09637480802498820
10. Bernardo, M L R and Azarcon, A C. (2012) A randomized controlled trial on the effects of oral collagen treatment on the medial joint space and functional outcome among Veterans Memorial Medical Center patients diagnosed with osteoarthritis of the knee. *PARM Proceedings,* 4, 1-8.
11. Trojian, T H., Concoff, A L., Joy, S M., Hatzenbuehler, J R., Saulsberry, W J., and Coleman, C I. (2016) AMSMM scientific statement concerning viscosupplementation injections for knee osteoarthritis: Importance for individual patient outcomes. *British Journal of Sports Medicine,* 50, 84-92. doi:10.1136/bjsports-2015-095683
12. Gregory, P J and Fellner, C. (2014). Dietary supplements as disease-modifying treatments in osteoarthritis: A critical appraisal. *Pharmacology & Therapeutics,* 39 (6), 436-452.
13. Elder S H, Borazjani A. Effect of collagen hydrolysate on chondrocyte-seeded agarose constructs. Biomed Mater Eng 2009; 19(6):409-14.
14. Ng K W, Saliman J D, Lin E Y, Statman L Y, Kugler L E, Lo S B, et al. Culture duration modulates collagen hydrolysate-induced tissue remodeling in chondrocyte-seeded agarose hydrogels. Ann Biomed Eng 2007; 35 (November (11)):1914-23.
15. Bello A E, Oesser S. Collagen hydrolysate for the treatment of osteoarthritis and other joint disorders: a review of the literature. Curr Med Res Opin 2006; 22 (November (11)): 2221-32.
16. Oesser S, Seifert J. Stimulation of type II collagen biosynthesis and secretion in bovine chondrocytes cultured with degraded collagen. Cell Tissue Res 2003; 311 (March (3)):393-9.

The invention claimed is:

1. A method for preventing and/or reducing joint pain in a patient having osteoarthritis, comprising administering to said patient a composition consisting of a collagen hydrolysate, gelatin, and vegetable magnesium stearate, wherein the collagen hydrolysate has a molecular weight of less than 1500 daltons.

2. A method for increasing a cartilage abrasion grade and reducing a lateral meniscal protrusion in a patient's knee, comprising administering to said patient a composition consisting of a collagen hydrolysate, gelatin, and vegetable magnesium stearate, wherein the collagen hydrolysate has a molecular weight of less than 1500 daltons, and wherein the composition docs not comprise any of hyaluronic acid, chondroitin, and vitamin C.

3. The method of claim 1, wherein the daily dosage of the collagen hydrolysate is between 1000 and 2000 mg.

4. The method of claim 1, wherein the prevention and/or reduction of the joint pain lasts more than 3 months.

5. The method of claim 1, wherein the collagen hydrolysate has a molecular weight of less than 1400, 1300, 1200, 1100, 1000, 950, 900, 850, 800, 750, 700, 650 or 600 daltons.

6. The method of claim 1, wherein the collagen hydrolysate is in a solid, gel or liquid form.

7. The method of claim 1, wherein the joint pain is shoulder, elbow, hand, lumbar spine, hip or knee pain.

8. The method of claim 1, wherein the collagen hydrolysate is prepared from beef, pork, poultry, or fish skins or scales.

9. The method of claim 1, wherein the source of collagen is skin, hides, or bone.

10. The method of claim 1, wherein the patient is older than 50, 55, 60, 65, 70, 75, 80, 85, or 90 years.

11. The method of claim 1, wherein the patient is a woman.

12. The method of claim 1, wherein the collagen hydrolysate has no bitter taste or odor.

13. The method of claim 3, wherein the daily dosage of the collagen hydrolysate is between 1000 and 2000 mg.

14. The method of claim 3, wherein the collagen hydrolysate has a molecular weight of less than 1400, 1300, 1200, 1100, 1000, 950, 900, 850, 800, 750, 700, 650 or 600 daltons.

15. The method of claim 3, wherein the collagen hydrolysate is in a solid, gel or liquid form.

16. The method of claim 2, wherein the collagen hydrolysate is prepared from beef, pork, poultry, or fish skins or scales.

17. The method of claim 16, wherein the source of collagen is skin, hides, or bone.

18. The method of claim 2, wherein the patient is older than 50, 55, 60, 65, 70, 75, 80, 85, or 90 years.

19. The method of claim 2, wherein the patient is a woman.

20. The method of claim 2, wherein the collagen hydrolysate has no bitter taste or odor.

21. A method for preventing and/or reducing joint pain in a patient having osteoarthritis, comprising administering to said patient a composition consisting of a collagen hydrolysate, gelatin, vegetable magnesium stearate, and microcrystalline cellulose or silicon dioxide, wherein the collagen hydrolysate has a molecular weight of less than 1500 daltons.

22. A method for increasing a cartilage abrasion grade and reducing a lateral meniscal protrusion in a patient's knee, comprising administering to said patient a composition consisting of a collagen hydrolysate, gelatin, vegetable magnesium stearate, and microcrystalline cellulose or silicon dioxide, wherein the collagen hydrolysate has a molecular weight of less than 1500 daltons.

* * * * *

UNITED STATES PATENT AND TRADEMARK OFFICE
CERTIFICATE OF CORRECTION

PATENT NO. : 11,040,081 B2  
APPLICATION NO. : 16/463985  
DATED : June 22, 2021  
INVENTOR(S) : Guy Michaud Page 1 of 1

It is certified that error appears in the above-identified patent and that said Letters Patent is hereby corrected as shown below:

In the Claims

In Claim 2, Column 29, Lines 36-38, ", and wherein the composition docs not comprise any of hyaluronic acid, chondroitin, and vitamin C" should be deleted.

Signed and Sealed this  
Tenth Day of August, 2021

Drew Hirshfeld  
*Performing the Functions and Duties of the*  
*Under Secretary of Commerce for Intellectual Property and*  
*Director of the United States Patent and Trademark Office*